United States Patent [19]
Hirano et al.

[11] Patent Number: 5,869,087
[45] Date of Patent: Feb. 9, 1999

[54] PATCH HAVING A PREPARATION FOR EXTERNAL USE ATTACHED THERETO

[75] Inventors: Munehiko Hirano, Tsukuba; Kiyomi Tsuruta, Tosu, both of Japan

[73] Assignee: Hisamitsu Pharmaceutical Co., Inc., Tosu, Japan

[21] Appl. No.: 793,692

[22] PCT Filed: Sep. 11, 1995

[86] PCT No.: PCT/JP95/01798

§ 371 Date: Feb. 27, 1997

§ 102(e) Date: Feb. 27, 1997

[87] PCT Pub. No.: WO96/08245

PCT Pub. Date: Mar. 21, 1996

[30] Foreign Application Priority Data

Sep. 16, 1994 [JP] Japan .................................. 6-248814

[51] Int. Cl.$^6$ .................................................... A61F 13/00
[52] U.S. Cl. ............................................ 424/449; 514/969
[58] Field of Search ............................. 424/449; 514/969

[56] References Cited

U.S. PATENT DOCUMENTS

| | | | |
|---|---|---|---|
| 4,491,592 | 1/1985 | Katoh | 424/318 |
| 4,545,992 | 10/1985 | Kamishita | 514/161 |
| 4,740,365 | 4/1988 | Yukimatsu | 424/435 |
| 5,176,916 | 1/1993 | Yamanaka | 424/448 |
| 5,322,685 | 6/1994 | Nakagawa | 424/78.03 |
| 5,519,046 | 5/1996 | Noda | 514/413 |

*Primary Examiner*—D. Gabrielle Brouillette
*Attorney, Agent, or Firm*—Kubovcik & Kubovcik

[57] ABSTRACT

A preparation for external use in application to the body, which comprises an antiphlogistic with carboxylic groups in the molecule, l-menthol and a metal salt of a fatty acid; and a patch having the preparation spread thereon for easier application to the body.

17 Claims, 1 Drawing Sheet

FIG. 1

PATCH HAVING A PREPARATION FOR EXTERNAL USE ATTACHED THERETO

This application is a 371 of PCT/JP95/01798, filed Sep. 11, 1995.

TECHNICAL FIELD

This invention relates to a preparation for external use comprising an anti-inflammatory or antiphlogistic with carboxylic groups in the molecule, l-menthol and a metal salt of a fatty acid, and it also relates to a patch having the preparation spread thereon. More particularly, it relates to a novel preparation comprising an antiphlogistic with carboxylic groups in the molecule, l-menthol as a solubilizer for the antiphlogistic or as a medicinally efficacious ingredient or a cooling agent, and a fatty acid metal salt as a stabilizer or esterification preventer for the antiphlogistic, and it also relates to a novel patch having the preparation spread thereon.

BACKGROUND ART

Attempts to use in therapies a so-called preparation-on-tape wherein an antiphlogistic is made to be contained in an oily adhesive, have widely been made; for example, Japanese Pat. Appln. Laid-Open Gazette No. 59-227819 (No. 227819/84) discloses that a non-steroidal anti-inflammatory analgesic is made to be contained in an acrylic pressure-sensitive adhesive applied on a composite composed of a non-woven cloth and a film, for an attempt to be administered to patients. Japanese Pat. Appln. Laid-Open Gazette No. 60-139615 (No. 139615/85) discloses that ketoprofen contained in an adhesive composed of a polyisobutylene/paraffin/rosin-modified glycerol ester is attempted to be percutaneously absorbed into patients. Japanese Pat. Appln. Laid-Open Gazette No. 63-227524 (No. 227524/88) discloses that flurbiprofen contained in an oily base is attempted to be administered to patients. Further, Japanese Pat. Appln. Laid-Open Gazette No. 64-40420 (No. 40420/89) discloses that a non-steroidal anti-inflammatory analgesic with carboxyl groups in the molecule contained in an oily base is attempted to be administered. Any of the above attempts, however, did not achieve satisfactory release and percutaneous absorbability of the drug. Thus, further excellent preparations have been sought for.

It was previously disclosed in the International Pat. Appln. (Publication No. WO 93/04677) filed by the same applicant as that of this invention that a preparation-on-tape composed of a non-steroidal anti-inflammatory analgesic such as ketoprofen, a rosin ester derivative and l-menthol as a solubilizer exhibited a great increase in percutaneous absorbability of the drug. Although the above preparation-on-tape so disclosed achieved initial objects such as a great increase in percutaneous absorbability and releasability of the drug, a decrease in side effects such as skin rash caused by repeated application of the tape to the skin and the expedient usability of the drug at the place of remedy, it has thereafter been found that the non-steroidal anti-inflammatory analgesic as the main drug is reacted with l-menthol used as a solubilizer to produce a l-menthol ester whereby is raised a problem particularly as to the stability and the like of the main drug.

The object of this invention is to provide a preparation for external use wherein particularly an anti-inflammatory drug maintains its stability while maintaining satisfactory releasability and percutaneous absorbability of the drug, and also to provide a patch having said preparation attached thereto.

DISCLOSURE OF THE INVENTION

The present inventors made intensive studies in an attempt to achieve the above object of this invention and, as the result of their studies, found that a formulation obtained by combining an anti-inflammatory drug having carboxylic groups in the molecule and l-menthol as a solubilizer for the drug or as a medicinally efficacious ingredient or cooling agent, will surprisingly be much improved in the stability and esterification preventability of the drug while maintaining the high releasability and percutaneous absorbability thereof, by adding a metal salt of a fatty acid to said formulation thereby to obtain a preparation of this invention.

In summary, this invention resides principally in a preparation for external use which comprises as the essential components:

(a) an antiphlogistic having carboxylic groups in the molecule, (b) l-menthol as a solubilizer for the antiphlogistic, or as a medicinally efficacious ingredient or cooling agent for the preparation, and (c) a metal salt of a fatty acid, as a stabilizer and esterification preventer for the drug. Further, this invention relates to a preparation for external use which comprises an adhesive in addition to the above essential components.

The particular characteristic of this invention resides in the use of the fatty acid metal salt as the stabilizer and esterification preventer for the drug in spite of the fact that said fatty acid metal salt has conventionally been recognized as a lubricant in the field of cosmetics such as baby powder and a perspiration suppressant by those skilled in said field.

The antiphlogistic with carboxylic groups in the molecule and l-menthol as the solubilizer, medicinally efficacious ingredient or cooling agent are blended together in specified ratios thereby to produce a base wherein the antiphlogistic and l-menthol are made non-crystalline by mixing with each other and are solubilized in each other without their crystallization thereby to exhibit high releasability and consequent high percutaneous absorbability of the drug. On the other hand, the antiphlogistic (drug) and the l-menthol are reacted together with the lapse of time to produce a l-menthol ester. At this point, the present inventors succeeded in securing high stability of the drug only by preventing the drug from its esterifying reaction while allowing the drug to keep its high solubility in the base, releasability and percutaneous absorbability, by means of adding the fatty acid metal salt to the base resulting in forming the preparation of this invention. It was not until this invention was made that such a fatty acid metal salt was used as a stabilizer or an esterification preventer for such an antiphlogistic in such a preparation for external use of this invention. This finding is novel and is not known from conventional known literature etc.

The fatty acid of the fatty acid metal salt includes a long-chain fatty acid such as undecylenic acid, stearic acid, palmitic acid, myristic acid or lauric acid, and the metal salt thereof preferably includes a zinc salt, aluminum salt, calcium salt, magnesium salt or sodium salt. More particularly, the fatty acid metal salt preferably includes zinc undecylenate, zinc stearate, calcium stearate, aluminum stearate, magnesium stearate, sodium stearate, zinc palmitate, zinc myristate, magnesium myristate, sodium laurate or zinc laurate. These metal salts may be used singly or jointly, among which zinc stearate is particularly preferred.

The fatty acid metal salts described as standards of raw materials of cosmetics, in the Japanese Pharmacopoeia, BP (British Pharmacopoeia), USP (US Pharmacopoeia) or EP (European Pharmacopoeia) are particularly preferable ones.

The amount of the fatty acid metal salt contained in the preparation is preferably in a range of 0.5–10% by weight. If it is less than 0.5% by weight then the esterification-preventive effect on the antiphlogistic is difficultly obtainable whereby the percutaneous absorbability and pharmacological activity of the drug are greatly impaired, whereas if it is more than 10% by weight then the stability of the preparation is worsened and, in addition, the releasability and percutaneous absorbability or pharmacological activity of the drug is much impaired.

An adhesive which allows the preparation to be attached to bodies, is composed of an elastic material, a tackifier and a softener. These components may be suitably selected from known materials in view of safety for the skin, adhesiveness to the skin, and the like. For example, the elastic materials include natural rubber-based, synthetic rubber-based, silicone-based and acrylic-based materials. Among the synthetic rubber-based materials, a styrene-isoprene-styrene block copolymer is preferred.

The styrene-isoprene-styrene block copolymer includes Cariflex TR-1107, TR-1111, TR-1112 and TR-1117 (trade names, products of Shell Chemical Co., Ltd.), JSR SIS-5000 and 5002 (trade names, products of Japan Synthetic Rubber Co., Ltd.), QUINTAC 3530 and 3421 (trade names, products of NIPPON Zeon Co., Ltd.) and Solprene 428 (trade name, a product of Phillips Petroleum Co., Ltd.). As stated above, a styrene-isoprene-styrene block copolymer is preferably used as the base polymer in this invention. However, the copolymer may be used together with another polymer such as polyisobutylene or polyisoprene.

The tackifiers include polyterpene resins, petroleum resins, rosins, hydrogenated rosins, hydrogenated rosin esters and oil soluble phenol resins, among which rosins and hydrogenated rosin esters are preferred. Rosin ester derivatives refer to the products prepared by esterifying various rosins and subjecting the obtained esters to hydrogenation or purification. The esters include methyl esters, glycerol esters and pentaerythritol esters. The rosin ester derivatives include Ester Gum A, AA-G, H and HP (trade names, products of Arakawa Chemical Industry Co., Ltd.), Hariester-L, S and P (trade names, products of Harima Chemicals Co., Ltd.), Super Ester A-75 and S-100 (trade names, products of Arakawa Chemical Industry Co., Ltd.), Pine Crystal KE-100 (trade name, a product of Arakawa Chemical Industry Co., Ltd.), KE-311 (trade name, a product of Arakawa Chemical Industry Co., Ltd.), Hercolyn D (trade name, a product of Hercules Co., Ltd.) and Foral 85 and 105 (trade names, products of Hercules Co., Ltd.).

The softeners serve to plasticize or soften elastic materials represented by the styrene-isoprene-styrene block copolymer and tackifiers represented by the rosin ester derivative thereby to allow the preparation to keep proper adhesion to the skin. The softeners include almond oil, olive oil, camellia oil, persic oil, peanut oil, olefin acids and liquid paraffin, with liquid paraffin being particularly preferred. In this invention, it is particularly preferable that the styrene-isoprene-styrene block copolymer, rosin ester derivative and liquid paraffin be combined together to form an adhesive. When these three ingredients are mixed in a weight ratio of 100:15 to 300:100 to 500, the resultant adhesive will exhibit suitable adhesiveness to the skin.

The antiphlogistic having carboxylic groups in the molecule includes drugs which have such effects as anti-inflammation, analgesia or antirheumatism. Such drugs include salicylic acid, acetylsalicylic acid, flufenamic acid, mefenamic acid, acemetacin, alclofenac, diclofenac, ibuprofen, indomethacin, ketoprofen, loxoprofen, sulindac, tolmetin, lobenzarit, penicillamine, oxaprozin, diflunisal, fenbufen, fentiazac, flurbiprofen, naproxen, pranoprofen, tiaprofen, suprofen, felbinac, ketorolac, oxaprozin, etodolac and zaltoprofen. These drugs may be used singly or jointly, among which preferable are antiphlogistics having acetic groups or propionic groups in the molecule such as ketoprofen, indomethacin, flurbiprofen, ketorolac and felbinac in view of preventing esterification. It is desirable that the amount of the antiphlogistic used be 0.1 to 10% by weight, preferably 0.3 to 9% by weight and more preferably 0.5 to 8% by weight, of the preparation, though the amount is not particularly limited. The content of the antiphlogistic in the preparation is preferably 100 to 500 $\mu$g per cm$^2$ of a patch having the preparation spread thereon from the standpoints of therapeutically effective release of the drug and availability thereof.

Levo-menthol (l-menthol) is used in this invention as a solubilizer intended to dissolve the antiphlogistic, or as a medicinally efficacious adjuvant or a cooling agent intended to give a cooling effect, and is used in such an amount either as to attain all these purposes or as to correspond to each purpose. In particular, when l-menthol is used as the solubilizer for the antiphlogistic in the preparation of this invention, the content of l-menthol increases to some extent whereby the possibility of esterification of the drug tends to be stronger. Therefore, in a case where l-menthol is used as the solubilizer, it is more effective to use a fatty acid metal salt in the preparation of this invention.

The amount of l-menthol used is in a range of 0.1 to 20 weight %, preferably 0.5 to 15 weight % and more preferably 1.0 to 12 weight %, of the preparation.

In this invention, the mixing weight ratio among the antiphlogistic, l-menthol and fatty acid metal salt greatly influences the esterification-preventive effect of the salt on the drug. Therefore, l-menthol is incorporated in the antiphlogistic in a ratio by weight of 0.1 to 10 and preferably 0.5 to 5 based on the weight of the antiphlogistic; and the fatty acid metal salt is incorporated in the antiphlogistic in a ratio by weight of 0.1 to 7 and preferably 0.3 to 5 on the same basis as above, in order to increase the esterification-preventive effect on the drug.

It is needless to say that the preparation of this invention may contain additional ingredients such as inorganic fillers, plasticizers, antioxidants, UV absorbers, antihistamines, antibacterial agents and perfumes which have been publicly known in the art without any restriction, if required.

When the base used for the preparation of this invention is an anhydrous one, the esterification-preventive effect on the drug contained in the preparation tends to become conspicuous. Therefore, it is preferable that the preparation for external use have a substantially anhydrous formulation. Specifically, a plaster having an anhydrous formulation is the most preferable preparation form.

The preparation of this invention can be easily prepared by known processes. For example, according to a hot-melt process, the preparation can be obtained by mixing a styrene-isoprene-styrene block copolymer, a rosin ester derivative and a fatty acid metal salt with each other under heating at 120° to 160° C. by the use of a mixing machine such as a kneader or mixer and then adding an antiphlogistic and l-menthol to the resulting mixture thereby to form the preparation. Further, the patches of this invention can be manufactured by either spreading the resulting preparation directly on a backing, or spreading the preparation temporarily on a paper or film previously treated with a releasing agent, covering the spread preparation with a desired backing and thereafter pressing the whole to transfer the preparation on the paper or film to the backing thereby to obtain the patches. The patches of this invention can also be prepared by a solvent process which comprises dissolving such components as used in the invention in a solvent such as toluene, hexane or methylene chloride by the use of an explosion-proof mixer or mixing machine, spreading the obtained solution on a paper or film previously treated with a releasing agent, distilling off the solvent from the spread solution, covering the spread preparation with a desired backing and thereafter pressing the whole to transfer the preparation on the paper or film to the backing.

Effects

It has been found that the esterifying reaction between an antiphlogistic with carboxylic groups in the molecule as the main drug, and l-menthol in the preparation of this invention, is significantly depressed owing to the presence of a fatty acid metal salt in the preparation. Consequently, the preparation is enhanced in releasability and percutaneous absorbability of the antiphlogistic when used. Further, it has been found that the fatty acid metal salt also has a remarkable effect on stability of the drug.

BEST MODE FOR CARRYING OUT THE INVENTION

To further illustrate this invention in greater detail by reference to the following Examples, Comparative Examples, Reference Examples and Test Examples wherein all parts are by weight except for the Test Examples.

Example 1

| | |
|---|---|
| styrene/isoprene/styrene block copolymer (tradename: Cariflex TR-1107) | 24.0 parts |
| liquid paraffin | 68.0 parts |
| rosin ester derivative (tradename: Ester Gum H) | 5.0 parts |
| zinc stearate | 1.0 part |
| λ-menthol | 1.5 parts |
| ketoprofen | 0.5 parts |

In accordance with this formulation, a preparation and patches of this invention were produced respectively by the above-mentioned processes. Namely, the styrene/isoprene/styrene block copolymer was heated and mixed with the zinc stearate, softener and rosin ester derivative at a temperature of 120° to 160° C. in a kneader used as a mixing device to obtain a mixture. Subsequently, the thus obtained mixture was incorporated with the ketoprofen (non-steroidal antiphlogistic analgesic drug) and l-menthol and mixed together to obtain a preparation. The preparation so obtained was spread on a PET film previously treated with a releasing agent, covered with a polyester cloth (PET) and then cut into pieces each of a desired size thereby to obtain antiphlogistic analgesic patches of this invention.

Example 2

| | |
|---|---|
| styrene/isoprene/styrene block copolymer (tradename: Cariflex TR-1107) | 20.0 parts |
| liquid paraffin | 43.5 parts |
| rosin ester derivative (tradename: KE-311) | 28.5 parts |
| zinc stearate | 2.0 parts |
| λ-menthol | 3.0 parts |
| ketoprofen | 3.0 parts |

In accordance with this formulation, a preparation and patches were produced respectively by the same methods as described in Example 1.

Example 3

| | |
|---|---|
| styrene/isoprene/styrene block copolymer (tradename: Cariflex TR-1107) | 21.0 parts |
| liquid paraffin | 63.0 parts |
| rosin ester derivative (tradename: KE-311) | 8.0 parts |
| zinc stearate | 2.0 parts |
| λ-menthol | 4.0 parts |
| ketoprofen | 2.0 parts |

In accordance with this formulation, a preparation and patches were produced respectively by the same methods as described in Example 1.

Example 4

| | |
|---|---|
| styrene/isoprene/styrene block copolymer (tradename: Cariflex TR-1111) | 20.0 parts |
| polyisobutylene (mfd. by Exxon Chemical Co., Ltd.) | 10.0 parts |
| liquid paraffin | 58.0 parts |
| rosin ester derivative (tradename: Ester Gum H) | 7.0 parts |
| zinc stearate | 1.0 part |
| λ-menthol | 3.0 parts |
| ketoprofen | 1.0 part |

In accordance with this formulation, a preparation and patches were produced respectively by the same methods as described in Example 1.

Example 5

| | |
|---|---|
| styrene/isoprene/styrene block copolymer (tradename: Cariflex TR-1111) | 15.0 parts |
| polyisobutylene (mfd. by Exxon Chemical Co., Ltd.) | 5.0 parts |
| liquid paraffin | 23.0 parts |
| rosin ester derivative (tradename: Foral 85) | 37.0 parts |
| zinc stearate | 5.0 parts |
| λ-menthol | 10.0 parts |
| ketoprofen | 5.0 parts |

In accordance with this formulation, a preparation and patches were produced respectively by the same methods as described in Example 1.

Example 6

| | |
|---|---|
| styrene/isoprene/styrene block copolymer (tradename: Cariflex TR-1111) | 18.0 parts |
| polyisobutylene (mfd. by Exxon Chemical Co., Ltd.) | 9.0 parts |
| liquid paraffin | 44.5 parts |
| rosin ester derivative (tradename: Foral 105) | 16.5 parts |
| zinc stearate | 3.0 parts |
| λ-menthol | 6.0 parts |
| ketoprofen | 3.0 parts |

In accordance with this formulation, a preparation and patches were produced respectively by the same methods as described in Example 1.

Example 7

| | |
|---|---|
| styrene/isoprene/styrene block copolymer (tradename: Solprene 418) | 28.0 parts |
| polybutene | 6.5 parts |
| liquid paraffin | 57.7 parts |
| rosin ester derivative (tradename: KE-311) | 5.0 parts |
| zinc stearate | 0.5 parts |
| λ-menthol | 1.8 parts |
| flurbiprofen | 0.5 parts |

In accordance with this formulation, a preparation and patches were produced respectively by the same methods as described in Example 1.

Example 8

| | |
|---|---|
| styrene/isoprene/styrene block copolymer (tradename: Cariflex TR-1107) | 21.0 parts |
| liquid paraffin | 65.3 parts |
| rosin ester derivative (tradename: KE-311) | 8.0 parts |
| zinc stearate | 3.5 parts |
| λ-menthol | 1.2 parts |
| flurbiprofen | 1.0 part |

In accordance with this formulation, a preparation and patches were produced respectively by the same methods as described in Example 1.

Example 9

| | |
|---|---|
| styrene/isoprene/styrene block copolymer (tradename: Cariflex TR-1107) | 7.0 parts |
| styrene/isoprene/styrene block copolymer (tradename: Cariflex TR-1111) | 7.0 parts |
| liquid paraffin | 44.0 parts |
| zinc stearate | 10.0 parts |
| rosin ester derivative (tradename: Super Ester S-100) | 20.0 parts |
| λ-menthol | 7.0 parts |
| flurbiprofen | 5.0 parts |

In accordance with this formulation, a preparation and patches were produced respectively by the same methods as described in Example 1.

Example 10

| | |
|---|---|
| styrene/isoprene/styrene block copolymer (tradename: Cariflex TR-1107) | 30.0 parts |
| liquid paraffin | 56.0 parts |
| zinc stearate | 2.0 parts |
| rosin ester derivative (tradename: KE-311) | 8.0 parts |
| λ-menthol | 3.0 parts |
| flurbiprofen | 1.0 part |

In accordance with this formulation, a preparation and patches were produced respectively by the same methods as described in Example 1.

Example 11

| | |
|---|---|
| styrene/isoprene/styrene block copolymer (tradename: Cariflex TR-1111) | 12.0 parts |
| liquid paraffin | 26.0 parts |
| zinc stearate | 6.0 parts |
| rosin ester derivative (tradename: Ester Gum H) | 36.0 parts |
| λ-menthol | 12.0 parts |
| flurbiprofen | 8.0 parts |

In accordance with this formulation, a preparation and patches were produced respectively by the same methods as described in Example 1.

Example 12

| | |
|---|---|
| styrene/isoprene/styrene block copolymer (tradename: Cariflex TR-1112) | 21.0 parts |
| liquid paraffin | 50.0 parts |
| zinc stearate | 2.0 parts |
| rosin ester derivative (tradename: Ester Gum H) | 20.5 parts |
| λ-menthol | 3.5 parts |
| felbinac | 3.0 parts |

In accordance with this formulation, a preparation and patches were produced respectively by the same methods as described in Example 1.

Example 13

| | |
|---|---|
| styrene/isoprene/styrene block copolymer (tradename: Cariflex TR-1111) | 10.0 parts |
| liquid paraffin | 48.5 parts |
| zinc stearate | 2.0 parts |
| rosin ester derivative (tradename: KE-311) | 22.5 parts |
| λ-menthol | 10.0 parts |
| ketoprofen | 7.0 parts |

In accordance with this formulation, a preparation and patches were produced respectively by the same methods as described in Example 1.

Example 14

| | |
|---|---|
| styrene/isoprene/styrene block copolymer (tradename: Cariflex TR-1107) | 20.0 parts |

| | |
|---|---|
| liquid paraffin | 45.0 parts |
| zinc stearate | 2.0 parts |
| rosin ester derivative | 21.0 parts |
| (tradename: Ester Gum H) | |
| λ-menthol | 9.0 parts |
| felbinac | 3.0 parts |

In accordance with this formulation, a preparation and patches were produced respectively by the same methods as described in Example 1.

Example 15

| | |
|---|---|
| styrene/isoprene/styrene block copolymer | 22.0 parts |
| (tradename: Cariflex TR-1107) | |
| polyisobutylene | 5.0 parts |
| (mfd. by Exxon Chemical Co., Ltd.) | |
| liquid paraffin | 52.0 parts |
| zinc stearate | 2.0 parts |
| rosin ester derivative | 10.0 parts |
| (tradename: Hercolyn D) | |
| λ-menthol | 7.0 parts |
| flurbiprofen | 2.0 parts |

In accordance with this formulation, a preparation and patches were produced respectively by the same methods as described in Example 1.

Example 16

| | |
|---|---|
| styrene/isoprene/styrene block copolymer | 20.0 parts |
| (tradename: QUINTAC 3421) | |
| liquid paraffin | 38.0 parts |
| zinc stearate | 0.5 parts |
| rosin ester derivative | 29.5 parts |
| (tradename: KE-311) | |
| λ-menthol | 8.0 parts |
| flurbiprofen | 4.0 parts |

In accordance with this formulation, a preparation and patches were produced respectively by the same methods as described in Example 1.

Example 17

| | |
|---|---|
| styrene/isoprene/styrene block copolymer | 28.0 parts |
| (tradename: Cariflex TR-1107) | |
| liquid paraffin | 56.0 parts |
| zinc stearate | 3.5 parts |
| rosin ester derivative | 9.0 parts |
| (tradename: Foral 85) | |
| λ-menthol | 2.5 parts |
| ketorolac | 1.0 part |

In accordance with this formulation, a preparation and patches were produced respectively by the same methods as described in Example 1.

Example 18

| | |
|---|---|
| styrene/isoprene/styrene block copolymer | 18.0 parts |
| (tradename: Cariflex TR-1111) | |
| polyisobutylene | 10.0 parts |
| (mfd. by Exxon Chemical Co., Ltd.) | |
| liquid paraffin | 50.0 parts |
| zinc stearate | 2.0 parts |
| rosin ester derivative | 14.0 parts |
| (tradename: Ester Gum H) | |
| λ-menthol | 4.0 parts |
| flurbiprofen | 2.0 parts |

In accordance with this formulation, a preparation and patches were produced respectively by the same methods as described in Example 1.

Example 19

| | |
|---|---|
| styrene/isoprene/styrene block copolymer | 16.5 parts |
| (tradename: Cariflex TR-1111) | |
| polyisobutylene | 8.5 parts |
| (mfd. by Exxon Chemical Co., Ltd.) | |
| liquid paraffin | 57.0 parts |
| zinc stearate | 1.0 part |
| rosin ester derivative | 15.0 parts |
| (tradename: Foral 105) | |
| λ-menthol | 1.5 parts |
| indomethacin | 0.5 parts |

In accordance with this formulation, a preparation and patches were produced respectively by the same methods as described in Example 1.

Example 20

| | |
|---|---|
| styrene/isoprene/styrene block copolymer | 17.5 parts |
| (tradename: Cariflex TR-1111) | |
| polyisobutylene | 9.5 parts |
| (mfd. by Exxon Chemical Co., Ltd.) | |
| liquid paraffin | 50.0 parts |
| zinc stearate | 2.0 parts |
| rosin ester derivative | 15.0 parts |
| (tradename: KE-311) | |
| benzophenone | 1.0 part |
| λ-menthol | 3.0 parts |
| ketoprofen | 2.0 parts |

In accordance with this formulation, a preparation and patches were produced respectively by the same methods as described in Example 1.

Example 21

| | |
|---|---|
| styrene/isoprene/styrene block copolymer | 17.0 parts |
| (tradename: JSR SIS-5002) | |
| polyisobutylene | 10.0 parts |
| (mfd. by Exxon Chemical Co., Ltd.) | |
| liquid paraffin | 49.0 parts |
| zinc stearate | 2.0 parts |
| rosin ester derivative | 16.0 parts |
| (tradename: Pine Crystal KE-100) | |
| benzophenone | 1.0 part |
| λ-menthol | 3.0 parts |
| ketoprofen | 2.0 parts |

In accordance with this formulation, a preparation and patches were produced respectively by the same methods as described in Example 1.

Example 22

| | |
|---|---|
| styrene/isoprene/styrene block copolymer (tradename: Cariflex TR-1107) | 20.0 parts |
| liquid paraffin | 43.5 parts |
| rosin ester derivative (tradename: KE-311) | 28.5 parts |
| zinc palmitate | 2.0 parts |
| λ-menthol | 3.0 parts |
| ketoprofen | 3.0 parts |

In accordance with this formulation, a preparation and patches were produced respectively by the same methods as described in Example 1.

Example 23

| | |
|---|---|
| styrene/isoprene/styrene block copolymer tradename: Cariflex TR-1107) | 21.0 parts |
| liquid paraffin | 63.0 parts |
| rosin ester derivative (tradename: KE-311) | 8.0 parts |
| aluminum stearate | 2.0 parts |
| λ-menthol | 4.0 parts |
| ketoprofen | 2.0 parts |

In accordance with this formulation, a preparation and patches were produced respectively by the same methods as described in Example 1.

Example 24

| | |
|---|---|
| styrene/isoprene/styrene block copolymer (tradename: Cariflex TR-1111) | 15.0 parts |
| polyisobutylene (mfd. by Exxon Chemical Co., Ltd.) | 5.0 parts |
| liquid paraffin | 23.0 parts |
| rosin ester derivative (tradename: Foral 85) | 37.0 parts |
| zinc undecylenate | 3.0 parts |
| zinc palmitate | 2.0 parts |
| λ-menthol | 10.0 parts |
| ketoprofen | 5.0 parts |

In accordance with this formulation, a preparation and patches were produced respectively by the same methods as described in Example 1.

Example 25

| | |
|---|---|
| styrene/isoprene/styrene block copolymer (tradename: Cariflex TR-1111) | 18.0 parts |
| polyisobutylene (mfd. by Exxon Chemical Co., Ltd.) | 9.0 parts |
| liquid paraffin | 44.5 parts |
| rosin ester derivative (tradename: Foral 105) | 16.5 parts |
| calcium stearate | 3.0 parts |
| λ-menthol | 6.0 parts |
| ketoprofen | 3.0 parts |

In accordance with this formulation, a preparation and patches were produced respectively by the same methods as described in Example 1.

Example 26

| | |
|---|---|
| styrene/isoprene/styrene block copolymer (tradename: Solprene 418) | 28.0 parts |
| polybutene | 6.5 parts |
| liquid paraffin | 57.7 parts |
| rosin ester derivative (tradename: KE-311) | 5.0 parts |
| zinc laurate | 0.5 parts |
| λ-menthol | 1.8 parts |
| flurbiprofen | 0.5 parts |

In accordance with this formulation, a preparation and patches were produced respectively by the same methods as described in Example 1.

Example 27

| | |
|---|---|
| styrene/isoprene/styrene block copolymer (tradename: Cariflex TR-1107) | 21.0 parts |
| liquid paraffin | 65.3 parts |
| rosin ester derivative (tradename: KE-311) | 8.0 parts |
| zinc myristate | 2.5 parts |
| zinc stearate | 1.0 part |
| λ-menthol | 1.2 parts |
| flurbiprofen | 1.0 part |

In accordance with this formulation, a preparation and patches were produced respectively by the same methods as described in Example 1.

Example 28

| | |
|---|---|
| styrene/isoprene/styrene block copolymer (tradename: Cariflex TR-1107) | 7.0 parts |
| styrene/isoprene/styrene block copolymer (tradename: Cariflex TR-1111) | 7.0 parts |
| liquid paraffin | 44.0 parts |
| magnesium stearate | 5.0 parts |
| magnesium myristate | 5.0 parts |
| rosin ester derivative (tradename: Super Ester S-100) | 20.0 parts |
| λ-menthol | 7.0 parts |
| flurbiprofen | 5.0 parts |

In accordance with this formulation, a preparation and patches were produced respectively by the same methods as described in Example 1.

Example 29

| | |
|---|---|
| styrene/isoprene/styrene block copolymer (tradename: Cariflex TR-1107) | 30.0 parts |
| liquid paraffin | 56.0 parts |
| sodium stearate | 2.0 parts |
| rosin ester derivative (tradename: KE-311) | 8.0 parts |
| λ-menthol | 3.0 parts |
| flurbiprofen | 1.0 part |

In accordance with this formulation, a preparation and patches were produced respectively by the same methods as described in Example 1.

Example 30

| | |
|---|---|
| styrene/isoprene/styrene block copolymer (tradename: Cariflex TR-1111) | 12.0 parts |
| liquid paraffin | 26.0 parts |
| magnesium myristate | 6.0 parts |
| rosin ester derivative (tradename: Ester Gum H) | 36.0 parts |
| λ-menthol | 12.0 parts |
| flurbiprofen | 8.0 parts |

In accordance with this formulation, a preparation and patches were produced respectively by the same methods as described in Example 1.

Example 31

| | |
|---|---|
| styrene/isoprene/styrene block copolymer (tradename: Cariflex TR-1112) | 21.0 parts |
| liquid paraffin | 50.0 parts |
| zinc undecylenate | 2.0 parts |
| rosin ester derivative (tradename: Ester Gum H) | 20.5 parts |
| λ-menthol | 3.5 parts |
| felbinac | 3.0 parts |

In accordance with this formulation, a preparation and patches were produced respectively by the same methods as described in Example 1.

Example 32

| | |
|---|---|
| styrene/isoprene/styrene block copolymer (tradename: Cariflex TR-1111) | 10.0 parts |
| liquid paraffin | 48.5 parts |
| calium stearate | 2.0 parts |
| rosin ester derivative (tradename: KE-311) | 22.5 parts |
| l-menthol | 10.0 parts |
| ketoprofen | 7.0 parts |

In accordance with this formulation, a preparation and patches were produced respectively by the same methods as described in Example 1.

Example 33

| | |
|---|---|
| styrene/isoprene/styrene block copolymer (tradename: Cariflex TR-1107) | 20.0 parts |
| liquid paraffin | 45.0 parts |
| sodium laurate | 2.0 parts |
| rosin ester derivative (tradename: Ester Gum H) | 21.0 parts |
| l-menthol | 9.0 parts |
| felbinac | 3.0 parts |

In accordance with this formulation, a preparation and patches were produced respectively by the same methods as described in Example 1.

Example 34

| | |
|---|---|
| styrene/isoprene/styrene block copolymer (tradename: Cariflex TR-1107) | 22.0 parts |
| polyisobutylene (mfd. by Exxon Chemical Co., Ltd.) | 5.0 parts |
| liquid paraffin | 52.0 parts |
| aluminum stearate | 2.0 parts |
| rosin ester derivative (tradename: Hercolyn D) | 10.0 parts |
| l-menthol | 7.0 parts |
| flurbiprofen | 2.0 parts |

In accordance with this formulation, a preparation and patches were produced respectively by the same methods as described in Example 1.

Example 35

| | |
|---|---|
| styrene/isoprene/styrene block copolymer (tradename: QUINTAC 3421) | 20.0 parts |
| liquid paraffin | 38.0 parts |
| zinc palmitate | 0.5 parts |
| rosin ester derivative (tradename: KE-311) | 29.5 parts |
| l-menthol | 8.0 parts |
| flurbiprofen | 4.0 parts |

In accordance with this formulation, a preparation and patches were produced respectively by the same methods as described in Example 1.

Comparative Example 1

Patches were produced by using the same composition and production method as described in Example 4 except that no zinc stearate was added.

Comparative Example 2

Patches were produced by using the same composition and production method as described in Example 17 except that no zinc stearate was added.

Comparative Example 3

Patches were produced by using the same composition and production method as described in Example 18 except that no zinc stearate was added.

Comparative Example 4

Patches were produced by using the same composition and production method as described in Example 19 except that no zinc stearate was added.

Comparative Example 5

Patches were produced by using the same composition and production method as described in Example 20 except that no zinc stearate was added.

Comparative Example 6

Patches were produced by using the same composition and production method as described in Example 4 except that no l-menthol was added.

Comparative Example 7

| | |
|---|---|
| styrene/isoprene/styrene block copolymer (tradename: Cariflex TR-1111) | 18.0 parts |
| polyisobutylene (mfd. by Exxon Chemical Co., Ltd.) | 9.8 parts |
| liquid paraffin | 51.0 parts |
| zinc stearate | 0.2 parts |
| rosin ester derivative (tradename: KE-311) | 15.0 parts |
| benzophenone | 1.0 part |
| l-menthol | 3.0 parts |
| ketoprofen | 2.0 parts |

Patches were produced by the same way as described in Example 21 except that the content of zinc stearate was changed to 0.2 parts.

Comparative Example 8

| | |
|---|---|
| styrene/isoprene/styrene block copolymer (tradename: Cariflex TR-1111) | 16.0 parts |
| polyisobutylene (mfd. by Exxon Chemical Co., Ltd.) | 8.5 parts |
| liquid paraffin | 44.5 parts |
| zinc stearate | 11.0 parts |
| rosin ester derivative (tradename: KE-311) | 14.0 parts |
| benzophenone | 1.0 part |
| l-menthol | 3.0 parts |
| ketoprofen | 2.0 parts |

Patches were produced by the same way as described in Example 21 except that the content of zinc stearate was changed to 11.0 parts.

Referential Example 1

97 parts of an acrylic adhesive Nissetsu PE-300 (tradename, mfd. by Nippon Carbide Industries Co., Ltd.) were mixed with 3 parts of ketoprofen to obtain a preparation. The preparation so obtained was spread on a polyester film previously treated with a releasing agent, covered with a backing and then cut into pieces each of a desired size thereby to obtain patches.

Referential Example 2

Patches were produced by using the same composition and production method as described in Referential Example 1 except that the ketoprofen was replaced by flurbiprofen.

Test Example 1

(Stability Test)

A stability test was effected on each of the patches of Examples 4 and 17 to 21 and Comparative Examples 1 to 5 and 7 to 8 by storing each patch for two months at 60° C. and thereafter measuring the amount of a l-menthol ester generated. Table 1 summarizes the results.

TABLE 1

| Ex. No. | Amount of λ-menthol ester (%) | Amount of remaining drug (%) |
|---|---|---|
| Ex. 4 | 0.85 | 99.15 |
| Ex. 17 | 0.17 | 99.83 |

TABLE 1-continued

| Ex. No. | Amount of λ-menthol ester (%) | Amount of remaining drug (%) |
|---|---|---|
| Ex. 18 | 0.30 | 99.70 |
| Ex. 19 | 0.10 | 99.90 |
| Ex. 20 | 0.50 | 99.50 |
| Ex. 21 | 0.48 | 99.52 |
| Comp. Ex. 1 | 17.00 | 83.00 |
| Comp. Ex. 2 | 14.10 | 85.90 |
| Comp. Ex. 3 | 9.85 | 90.15 |
| Comp. Ex. 4 | 6.30 | 93.70 |
| Comp. Ex. 5 | 16.10 | 83.90 |
| Comp. Ex. 7 | 10.82 | 89.18 |
| Comp. Ex. 8 | 0.50 | 99.50 crystallization |

As apparent from Table 1, each of the patches of Examples 4 and 17 to 21 comprising zinc stearate which is a fatty acid metal salt, exhibited a great esterification-preventive effect on l-menthol and the drug contained in each patch was very high in stability, as compared with the patches of Comparative Examples 1 to 5 comprising no zinc stearate, that of Comparative Example 7 comprising 0.2 parts by weight of zinc stearate and that of Comparative Example 8 comprising 11 parts by weight of zinc stearate.

Test Example 2

(Test on Preparation for Stable Dissolubility of their Drugs)

The preparation of each of the patches of Examples 4 and 17 to 21 and Comparative Examples 6 to 8 was tested for stable dissolubility of their drugs by storing each patch for one month at 5° C. Table 2 summarizes the results.

TABLE 2

| Ex. No. | 5° C., 1 month | Conditions after the test |
|---|---|---|
| Ex. 4 | ⊚ | no change |
| Ex. 17 | ⊚ | no change |
| Ex. 18 | ⊚ | no change |
| Ex. 19 | ⊚ | no change |
| Ex. 20 | ⊚ | no change |
| Ex. 21 | ⊚ | no change |
| Comp. Ex. 6 | x | crystallization |
| Comp. Ex. 7 | x | crystallization |
| Comp. Ex. 8 | x | crystaiiization |

Test Example 3

(Test on Hairless Mouse for Permeation of Drug through its Skin)

Figure 1:
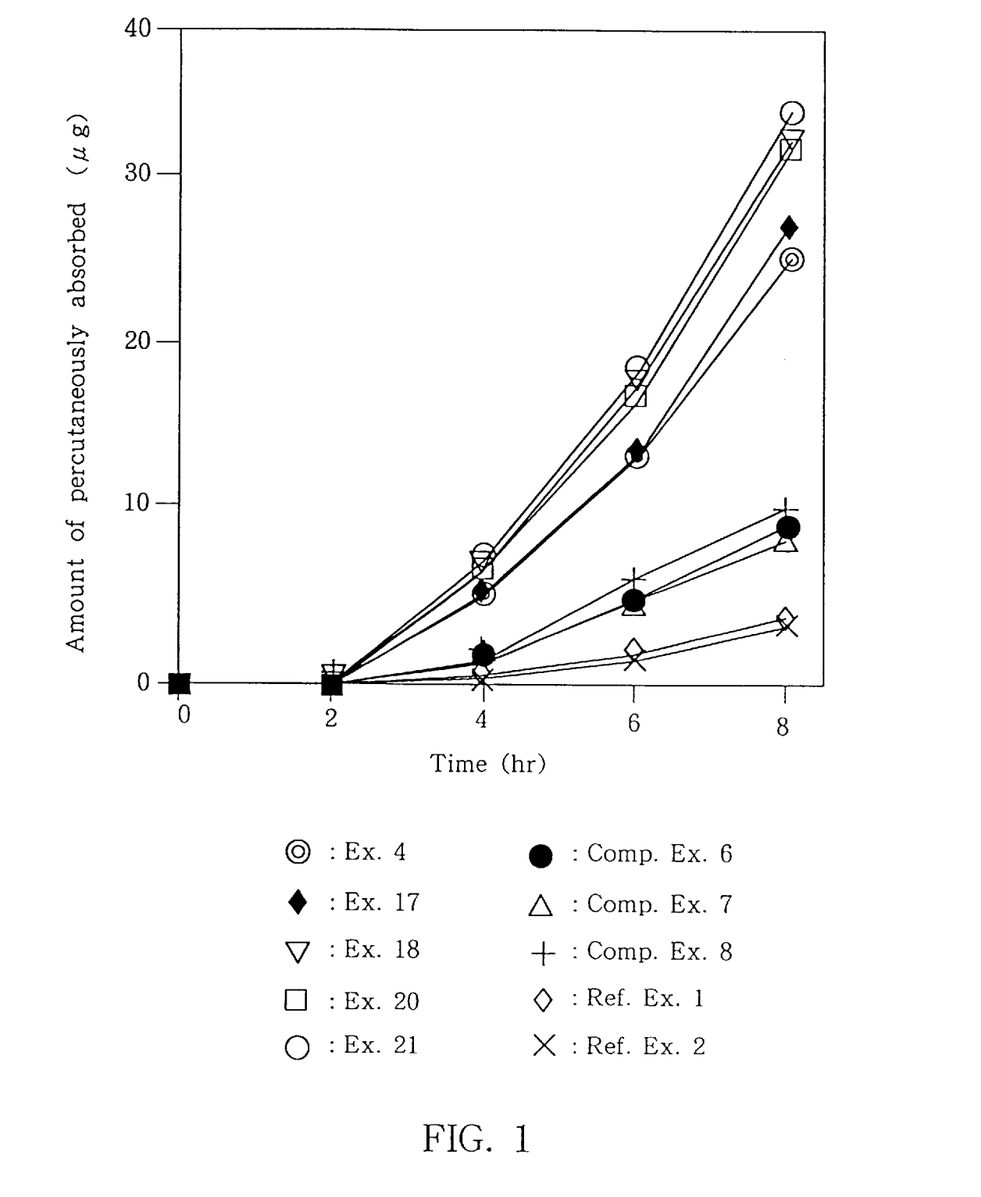
FIG. 1 is a graph respectively showing the results of tests on hairless mice for permeation of drugs through their skins.

The patches of Examples 4, 17 to 18 and 20 to 21, Comparative Examples 6 to 8 and Referential Examples 1 to 2 were each tested for permeation of the drug through hairless mouse skin. FIG. 1 shows the results.

As FIG. 1 shows, the patches of Examples 4, 17 to 18 and 20 to 21 were found to be obviously superior in release of the drug and percutaneous absorption of the drug (relative amount of the drug permeated) to those of Comparative Examples 6 to 8 and Referential Examples 1 to 2.

INDUSTRIAL APPLICABILITY

This invention has made it possible to significantly inhibit the amount of an ester formed by a chemical reaction between an antiphlogistic with carboxylic groups in the molecule and l-menthol, by means of adding a fatty acid metal salt to the drugs. That is, the ester which is not a medicinally efficacious ingredient but a by-product, is greatly inhibited from forming, with the result that the preparation of this invention is much enhanced in percutaneous absorbability and pharmacological activity of the antiphlogistic as the main drug. In addition, the releasability of the drug from the preparation becomes good. Thus it is very useful in the pharmaceutical industry to offer the preparation and the patch having the preparation attached thereto as pharmaceuticals against an inflammatory disease which fully exert the intended excellent remedial efficacy and are also more enhanced in safety when in use.

What is claimed is:

1. A patch for external use in application to the body, which comprises a plaster having a substantially anhydrous formulation and attached on a backing, the plaster comprising 1) an antiphlogistic with carboxylic groups in the molecule, 2) l-menthol and 3) a metal salt of a fatty acid.

2. A patch according to claim 1, wherein the l-menthol and the metal salt of a fatty acid are present in respective ratios by weight of 0.1–10 and 0.1–7 based on the weight of the antiphlogistic.

3. A patch according to claim 1 wherein the preparation further comprises an adhesive composed of an elastic material, a tackifier and a softener.

4. A patch according to claim 1, wherein the metal salt of a fatty acid is present in an amount by weight of 0.5–10% of the weight of the preparation.

5. A patch according to claim 1, wherein the metal salt of a fatty acid is used as a stabilizer or esterification preventer for the antiphlogistic.

6. A patch according to claim 1, wherein the metal salt of a fatty acid is selected from zinc undecylenate, zinc stearate, aluminum stearate, calcium stearate, magnesium stearate, sodium stearate, zinc palmitate, zinc myristate, magnesium myristate, zinc laurate and sodium laurate.

7. A patch according to claim 6, wherein the metal salt of a fatty acid is zinc stearate.

8. A patch according to claim 1, wherein the l-menthol is used as a solubilizer for the antiphlogistic.

9. A patch according to claim 1, wherein the antiphlogistic is selected from ketoprofen, indomethacin, flurbiprofen, ketorolac and felbinac.

10. A patch according to claim 1, wherein the antiphlogistic is present in an amount of 0.1 to 10% by weight of the preparation.

11. A patch according to claim 1, wherein the antiphlogistic is present in amount of 100 to 500 $\mu$g per $cm^2$ of the patch.

12. A patch according to claim 1, wherein the l-menthol is present in an amount of 0.1 to 20% by weight of the preparation.

13. A patch according to claim 3, wherein the elastic material is at least one member selected from the group consisting of styrene-isoprene-styrene block copolymers, polyisobutylene and polyisoprene.

14. A patch according to claim 3, wherein the tackifier is at least one member selected from the group consisting of polyterpene resins, petroleum resins, rosins, hydrogenated rosins, hydrogenated rosin esters and oil soluble phenol resins.

15. A patch according to claim 14, wherein the tackifier is at least one rosin ester derivative selected from the group consisting of methyl esters of a rosin, glycerol esters of a rosin and pentaerythritol esters of a rosin.

16. A patch according to claim 3, wherein the softener is at least one member selected from the group consisting of almond oil, olive oil, camellia oil, persic oil, peanut oil, olefin acids and liquid paraffin.

17. A patch according to claim 1, wherein the preparation further contains at least one member selected from the group consisting of inorganic fillers, plasticizers, antioxidants, UV absorbers, antihistamines, antibacterial agents and perfumes.

* * * * *